United States Patent [19]

Silbering et al.

[11] Patent Number: 4,477,429

[45] Date of Patent: Oct. 16, 1984

[54] ORAL COMPOSITIONS COMPRISING $N^\alpha$-ALKYL DERIVATIVES OF ARGININE

[75] Inventors: Steven B. Silbering, Plainsboro; Tibor Sipos, Lebanon, both of N.J.

[73] Assignee: Johnson & Johnson Products, Inc., New Brunswick, N.J.

[21] Appl. No.: 412,331

[22] Filed: Aug. 26, 1982

[51] Int. Cl.³ .................. A61K 7/22; C07C 129/12
[52] U.S. Cl. ................................ 424/52; 424/54; 562/560

[58] Field of Search .................. 562/560; 424/52, 54

Primary Examiner—Michael L. Shippen
Attorney, Agent, or Firm—Wayne R. Eberhardt

[57] ABSTRACT

Oral hygiene formulations incorporating $N^\alpha$-alkyl derivatives of arginine, or the pharmaceutically acceptable salts thereof, optionally in combination with fluoride compounds, are effective in combatting microorganisms, inhibiting acid production and reducing dental caries.

18 Claims, No Drawings

ORAL COMPOSITIONS COMPRISING N$^\alpha$-ALKYL DERIVATIVES OF ARGININE

FIELD OF THE INVENTION

The present invention relates to compositions of matter having utility in maintaining oral health. It also relates to methods of making such compositions, and the incorporation of same into pharmaceutically suitable vehicles for use in oral health care. More particularly, the invention relates to alkyl derivatives of arginine, optionally in combination with fluoride compounds, and their utility in maintaining oral health.

BACKGROUND OF THE INVENTION

It has been shown that tooth decay and dental disease can be attributed to bacteria forming plaque about the teeth. Growth and proliferation of bacteria is enhanced by the presence of entrapped food particles between the teeth. The removal of plaque and entrapped food particles reduces caries, reduces the tendency towards gingivitis, and reduces mouth odor as well as generally improving oral hygiene.

The prior art recognizes mechanical oral hygiene devices serving to clean the mouth of debris and remove plaque from teeth, such as toothbrushes, flosses, and toothpicks. It also recognizes compositions mostly used in conjunction with such devices but which impart a chemical action in cleaning teeth, such as dentifrices and rinses. In addition to these, various dental coatings and sealants have been applied to teeth as barriers against bacterial action and plaque formation. Another important approach in oral care includes the use of various fluoride-containing preparations which are able to deposit fluoride ions directly onto the surface of tooth enamel. While great advances were made in oral health care by the use of these various approaches, none seem to be completely effective.

A more recent approach to improved oral hygiene involves the recognition that bacteria present in the oral cavity metabolize dietary sugars, such as glucose and sucrose, to organic acids, such as acetic, propionic and lactic acids. The production of these acids results in a rapid drop in plaque pH. If the pH drops to a level of about 5.5 or below and remains there for more than a short period of time, the tooth enamel will begin to demineralize. This process, if repeated over a substantial period of time, will eventually lead to the development of caries. To correct for the pH drop, the saliva contains a pH-rise factor which moderates the extent and duration of the pH drop when glucose and sucrose are metabolized by oral bacteria. This factor was identified as an arginine-containing tetrapeptide. See, for example, Kleinberg, I., Kanapka, J. A., and Craw, D. "Effect of Saliva and Salivary Factors on the Metabolism of the Mixed Oral Flora" *Microbial Aspects of Dental Caries*, Vol. II, pp. 433-464 (1976). This pH-rise factor is believed to enter the bacterial cell and either neutralize the organic acids as they form or alter bacterial metabolism so that the acids are not produced.

DISCUSSION OF THE PRIOR ART

U.S. Pat. No. 2,689,170 to King, entitled "ORAL PREPARATION FOR INHIBITION OF DENTAL CARIES", discloses oral preparations for inhibition of dental caries having as the active ingredient a saturated higher series of alkyl acyl amide of a saturated aliphatic monoaminocarboxylic acid compound.

U.S. Pat. No. 4,154,813 to Kleinberg, entitled "MEANS AND METHOD FOR IMPROVING NATURAL DEFENSES AGAINST CARIES", discloses a method for supplementing the body's resistance to caries by providing a pH-rise factor which is a peptide of 2-4 amino acid units, one or more of which is arginine.

U.S. Pat. No. 4,225,579 to Kleinberg, entitled "MEANS AND METHOD FOR IMPROVING DEFENSES AGAINST CARIES", claims peptides of 2-4 amino acid units, one or more of which is arginine, for combatting caries. These arginine-containing peptides are disclosed to penetrate dental plaque and bacteria in the mouth and to counteract acid produced as a result of metabolism of carbohydrates.

British Pat. No. 1,352,420 to Yoshinaga et al, entitled "NOVEL ARGININE DERIVATIVES, THEIR PRODUCTION AND THEIR USE", discloses N$^\alpha$-acylarginines having antibacterial or germicidal properties for use in oral hygiene.

U.S. Pat. No. 3,809,759 to Bocher and Faure, entitled "PHARMACEUTICAL COMPOSITION FOR TREATING MENTAL FATIGUE CONTAINING ARGININE-POTASSIUM PHOSPHO-CITROGLUTAMATE AND METHOD OF USING THE SAME", discloses arginine-potassium phospho-citroglutamate in pharmaceutical compositions, such as, granules, pills, tablets, and capsules for systemic treatment of mental fatigue.

U.S. Pat. No. 4,061,542 to Demny and Maehr, entitled "2-METHYL-L-ARGININE PRODUCED BY CULTIVATING STREPTOMYCES STRAIN", discloses the title compound for use as an antibiotic and antibacterial agent.

U.S. Pat. No. 4,125,619 to Okamoto et al, entitled "N$^\alpha$-NAPHTHALENESULFONYL-L-ARGININE DERIVATIVES AND THE PHARMACEUTICALLY ACCEPTABLE ACID ADDITION SALTS THEREOF", discloses the title compounds for use as pharmaceutical agents for the inhibition and suppression of thrombosis.

The compounds of the present invention differ from the aforementioned prior art in that we use new and novel derivatives of arginine in which the polar character of the arginine molecule is modified by the presence of lipid-like substituents. This modification is believed to permit such arginine derivatives to more readily penetrate the phospholipid-containing cell wall of oral bacteria and to inhibit acid production of these bacteria.

Accordingly, one object of the present invention is to provide new and novel derivatives of arginine.

Another object of the present invention is to provide compositions containing an arginine derivative for use in oral applications.

Still another object of the present invention is to provide compositions containing an arginine derivative in combination with a fluoride compound for use in oral applications.

It is still a further object of the present invention to provide methods of preparing such compounds and compositions.

SUMMARY OF THE INVENTION

Oral compositions of the present invention comprise N$^\alpha$-alkyl derivatives of arginine of the formula:

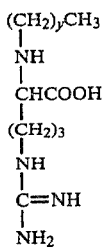

I where y is an integer from 6 to about 29, preferably from about 6 to about 19, and most preferably from 9 to 15.

The $N^\alpha$-alkyl derivatives of arginine where y is not more than about 19 are preferred since these derivatives possess greater activity against oral bacteria than the higher members of the series.

In general $N^\alpha$-alkyl derivatives of arginine may be prepared by combining L-(+)-arginine and an aliphatic aldehyde in a 1:1 mole ratio in an ethanol-water solution and agitating the mixture with hydrogen gas at about 2 atmospheres pressure in the presence of a palladium on carbon catalyst. When the reaction is complete, the mixture is filtered and the filtrate evaporated to dryness. The so-obtained crude product is purified by column chromatography using butanol-acetic acid-water (7:2:2) or other suitable system as the elution solvent.

The present invention also encompasses pharmaceutically acceptable salts of the $N^\alpha$-alkyl derivatives of arginine such as those formed by reaction of an organic or inorganic base with the acidic (—COOH) portion of the alkylarginine molecule, and those formed by reaction of an organic or inorganic acid with the basic amino or guanidino portions of the alkylarginine molecule. Typical salts are those of the formula

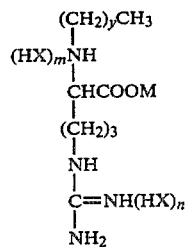

II wherein y is an integer of from 6 to about 29; M is H, Na, K, Mg, Ca, Ag, Ce, Mn, Zn or the residue of a strong organic base; m and n are 0 or 1; and HX is HCl, HNO$_3$, H$_2$SO$_4$, CH$_3$COOH or gluconic acid

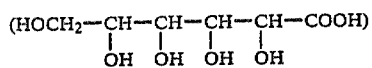

The present invention provides oral compositions of an $N^\alpha$-alkyl derivatives of arginine in the form of a mouthwash, spray, dentifrice, gel, powder, solution, lotion, varnish, lozenge, chewing gum, slow releasing device and the like for use in oral hygiene in combatting bacteria and to increase pH of the oral fluids.

The present invention further provides oral compositions of $N^\alpha$-alkyl derivatives of arginine in combination with a fluoride compound, such as, sodium fluoride, zinc fluoride, stannous fluoride, sodium monofluorophosphate, acidulated phosphate fluoride, ammonium fluoride, ammonium bifluoride and amine fluoride.

DETAILED DESCRIPTION OF THE INVENTION

The process for preparing compounds of this invention and oral compositions comprising such compounds are illustrated by the following specific examples, which are included for purposes of illustration only and are not intended to be limiting to the invention.

EXAMPLE 1

$N^\alpha$-decylarginine

L-(+)-arginine (5.54 g, 0.03180 mole) was dissolved in 25 ml of H$_2$O by warming on a steam bath. The pH was lowered from 11 to 7 by addition of 2.0 ml of glacial acetic acid. To this solution was added 200 ml of abs. ethanol. Decyl aldehyde (4.97 g, 0.03180 mole) was then added in one portion. To this mixture was added 0.26 g of 10% palladium on activated carbon catalyst suspended in 20 ml of abs. ethanol. The mixture was placed in a 500 ml pressure bottle and the bottle was attached to a Parr hydrogenator. The bottle was pressurized with hydrogen to 2 atmospheres and shaken at room temperature until the pressure dropped to 1 atmosphere. The bottle was repressurized to 2 atmospheres with hydrogen and shaking continued. This procedure was repeated until the hydrogen pressure remained constant. The contents of the bottle were then filtered through Celite, and the filtrate evaporated to dryness in a rotary evaporator at 45°. The residue was dissolved in 200 ml of H$_2$O and extracted with chloroform. An emulsion formed. In order to break the emulsion, saturated NaCl was added. The layers separated and the white chloroform layer was removed and evaporated to dryness, leaving a white solid. The solid was dissolved in boiling abs. ethanol and the hot solution was filtered. The filtrate was placed on a silica gel column (100 g silica gel), and the column was eluted using butanol-acetic acid-H$_2$O (4:1:1). The fractions containing the desired product were combined and evaporated to dryness in a rotary evaporator at 45°, and finally under vacuum overnight at room temperature to obtain a solid residue. The solid was extracted with ethyl acetate to remove residual n-butanol and recovered by filtration. The yield was 1.48 g, mp 100° C.

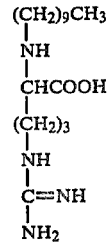

A similar procedure may be used to prepare the following $N^\alpha$-alkyl derivatives of arginine:
$N^\alpha$-octylarginine (C$_8$)
$N^\alpha$-nonylarginine (C$_9$)
$N^\alpha$-undecylarginine (C$_{11}$)
$N^\alpha$-laurylarginine (C$_{12}$)
$N^\alpha$-myristylarginine (C$_{14}$)
$N^\alpha$-palmitylarginine (C$_{16}$)
$N^\alpha$-stearylarginine (C$_{18}$)

Representative compounds of the present invention were assayed to determine their effectiveness in reducing acid production from sugar by *S. mutans* as a measure of their efficacy in oral compositions.

ASSAY FOR INHIBITORS OF GLYCOLYSIS

This assay measures the rate of acid production from the metabolism of sucrose by *Streptococcus mutans* 6715. The assay solution consists of 10.00 ml of a phosphate buffer at pH 5.5 under nitrogen. To this soltuion are added $8 \times 10^9$ cells of *S. mutans* 6715, followed by 50 μl of $25 \times 10^{-3}$M sucrose. A known volume of a 10 mg/ml solution of the test arginine derivative is then added, and the rate of acid production is monitored with the automatic addition of a $5 \times 10^{-3}$N KOH solution by a pH-stat.

Table I illustrates acid inhibition activity of the compounds indicated.

TABLE I

| Arginine Derivative | Concentration (W/V %) | Reduction in Rate of Acid Formation (%) |
|---|---|---|
| $N^\alpha$—octylarginine | 4.0 | 25 |
| $N^\alpha$—decylarginine | 4.0 | 50 |

Oral compositions of the present invention, include the combination of $N^\alpha$-alkyl derivatives of arginine with a fluoride compound, e.g. sodium fluoride, zinc fluoride, stannous fluoride, sodium monofluorophosphate, acidulated phosphate fluoride, ammonium fluoride, ammonium bifluoride and amine fluoride. In general, the $N^\alpha$-alkyl derivative of arginine should be present in an effective amount up to a saturated solution, while the fluoride ion should be present from as low as 0.0001% to 10%.

The preferred concentration of the $N^\alpha$-alkyl derivative of arginine is 0.05 to 10%, while that of the fluoride ion is 0.0001 to 1.0%. The most preferred concentration of $N^\alpha$-alkyl derivative of arginine is 0.5 to 5%, and the fluoride ion, 0.01 to 0.1%. While higher concentrations of both $N^\alpha$-alkyl derivatives of arginine and fluoride ions could be used, no particular advantage is afforded thereby.

While it is presently preferred to have a polyol-containing aqueous vehicle as an acceptable carrier for the above composition, other nonaqueous compositions are not excluded from the list of suitable carriers, as for example various alcohols, polyols, and dimethylsulfoxide.

The composition of this invention may be in the form of a mouthwash, spray, dentifrice, gel, powder, solution, lotion, varnish, lozenge, chewing gum, slow releasing device or other forms suitable for oral application. Any pharmaceutically acceptable materials such as those ordinarily used in such oral compositions that are compatible with $N^\alpha$-alkyl derivatives of arginine and fluoride ions may be employed in the compositions of this invention.

In accordance with the present invention, the compositions are supplied to teeth with an appliance, e.g., toothbrush, swab, impregnated dental floss and the like by gently brushing the teeth, both the buccal and lingual sides, at least once daily. The most preferred application of the above compositions to teeth is from lozenge and from chewing gum, whereby one slowly dissolves the lozenge in the mouth over 10 to 15 minutes, and by chewing the gum over 30 to 45 minutes after each meal.

The following examples will further serve to illustrate typical oral compositions of this invention.

EXAMPLE 2

(Mouthrinse)

| | w/w % |
|---|---|
| Glycerol, U.S.P. | 10 to 40 |
| $N^\alpha$—alkylarginine | 0.1 to 5 |
| NaF | 0.2 |
| Flavors | 1.0 |
| Preservatives | 0.3 |
| Pluronic F-108 | 2.0 |
| Water, q.s. to 100 parts | |

The $N^\alpha$-alkyl derivative of arginine was dissolved in water with continuous stirring at 80° C. The remaining ingredients were dissolved in glycerol and mixed with the $N^\alpha$-alkylarginine solution at room temperature.

EXAMPLE 3

(Gel Dentifrice)

| | w/w % |
|---|---|
| Pluronic F-127 | 20.0 |
| Flavors | 0.8 |
| Preservatives | 0.3 |
| $N^\alpha$—alkylarginine | 2.0 |
| Water, q.s. to 100 parts | |

EXAMPLE 4

(Gel Dentifrice)

| | w/w % |
|---|---|
| $N^\alpha$—alkylarginine | 2.0 |
| NaF | 0.2 |
| Pluronic F-127 | 20.0 |
| Flavors | 0.8 |
| Preservatives | 0.3 |
| Water, q.s. to 100 parts | |

The gels of Examples 3 and 4 were prepared as follows:

The $N^\alpha$-alkylarginine was dissolved in 50 ml water while continuously stirring at 80° C. After the arginine derivative had dissolved, the solution was cooled to room temperature and the NaF (if present) and preservatives were added. Separately, the Pluronic F-127 and flavors were dissolved at 4° C. The solution was allowed to warm up to room temperature and then blended into the arginine containing solution with continuous stirring. The mixture was homogenized and the pH of the gel adjusted to 5.5 by the addition of NaOH or HCl as required.

EXAMPLE 5

(Paste Dentifrice)

| | w/w % |
|---|---|
| $N^\alpha$—alkylarginine | 1 to 5 |
| NaF | 0.2 |
| Glycerol | 15.0 |
| Sorbitol | 10.0 |
| Sodium lauryl sulfate | 1.2 |

-continued

|  | w/w % |
| --- | --- |
| Calcium pyrophosphate | 40.0 |
| Propylene glycol | 10.0 |
| Flavors | 1.0 |
| Preservatives | 0.3 |
| Pluronic F-127 | 10.0 |
| Water, q.s. to 100 parts | |

The $N^\alpha$-alkylarginine was dissolved in glycerol, sorbitol, propylene glycol, Pluronic F-127 and water at 80° C. The pH was adjusted to 5.5 and the flavors, NaF, preservatives and sodium lauryl sulfate were added. The calcium pyrophosphate was blended into the mixture with continuous stirring at room temperature, and the mixture was homogenized with a roller mill. In this formulation, the sodium fluoride component is optional and may be omitted in the preparation of a non-fluoride dentifrice.

EXAMPLE 6

(Powder Dentifrice)

|  | w/w % |
| --- | --- |
| $N^\alpha$—alkylarginine | 1 to 5 |
| Flavors | 4.0 |
| Sodium lauryl sulfate | 2.0 |
| Saccharin | 0.4 |
| Abrasive q.s. to 100 parts | |

EXAMPLE 7

(Lozenge)

|  | w/w % |
| --- | --- |
| $N^\alpha$—alkylarginine | 1 to 5 |
| Sorbitol | 20.0 |
| Mannitol | 20.0 |
| Starch | 12.0 |
| Flavors | 2.0 |
| Preservatives | 0.4 |
| Saccharin | 0.2 |
| Magnesium stearate | 0.8 |
| Talc | 0.5 |
| Corn syrup, q.s. to 100 parts | |

The mixture of Example 7 was granulated into a homogeneous blend and pressed into a lozenge.

Although the present invention has been described with reference to particular embodiments and examples, it will be apparent to those skilled in the art that variations and modifications of this invention can be made and that equivalents can be substituted therefore without departing from the principles and the true spirit of the invention.

We claim:

1. $N^\alpha$-alkyl derivatives of arginine having the formula:

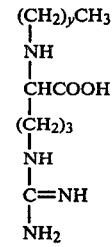

where y is an integer of from 6 to 29, and the pharmaceutically acceptable salts thereof.

2. A compound of claim 1 wherein said pharmaceutically acceptable salts are selected from the group consisting of alkali metal salts, alkaline earth metal salts, amphoteric metal salts, heavy metal salts, organic base salts, and organic and inorganic acid salts.

3. The compound of claim 1 wherein said $N^\alpha$-alkyl derivative of arginine is $N^\alpha$-octylarginine.

4. The compound of claim 1 wherein said $N^\alpha$-alkyl derivative of arginine is $N^\alpha$-decylarginine.

5. A composition of matter for oral hygiene to inhibit acid production by microorganisms in the oral cavity comprising an effective amount, in a pharmaceutically acceptable carrier, of an $N^\alpha$-alkyl derivative of arginine having the formula:

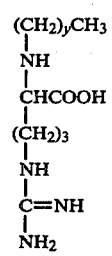

wherein y is an integer of from 6 to 29, or a pharmaceutically acceptable salt thereof.

6. The composition of matter of claim 5 wherein said $N^\alpha$-alkyl derivative of arginine is $N^\alpha$-octylarginine.

7. The composition of matter of claim 5 wherein said $N^\alpha$-alkyl derivative of arginine is $N^\alpha$-decylarginine.

8. The composition of matter of claim 5 wherein said pharmaceutically acceptable carrier is a dentifrice.

9. The composition of matter of claim 5 wherein said pharmaceutically acceptable carrier is a lozenge.

10. A composition of matter for oral hygiene to inhibit the formation of caries comprising, in a pharmaceutically acceptable carrier, from about 0.0001% to about 10% of a fluoride salt and an effective amount of an $N^\alpha$-alkyl derivative of arginine having the formula:

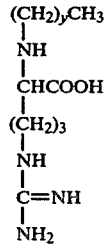

wherein y is an integer of from 6 to 29, or a pharmaceutically acceptable salt thereof.

11. The composition of matter of claim 10 wherein said pharmaceutically acceptable carrier is a mouthrinse.

12. The composition of matter of claim 10 wherein said pharmaceutically acceptable carrier is a dentifrice.

13. The composition of matter for oral hygiene to inhibit formation of caries comprising from about 0.05 to about 10% of $N^\alpha$-alkyl derivative of arginine having the formula:

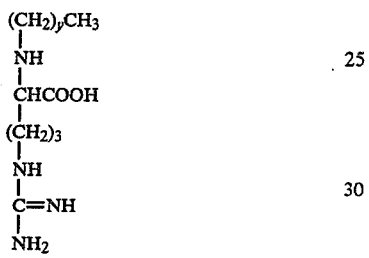

wherein y is an integer of from 6 to 19, or a pharmaceutically acceptable salt thereof, in combination with from about 0.001 to about 1.0% of a fluoride salt in a pharmaceutically acceptable polyol-containing vehicle.

14. The composition of matter of claim 13 wherein said $N^\alpha$-alkyl derivative of arginine is $N^\alpha$-octylarginine.

15. The composition of matter of claim 13 wherein said $N^\alpha$-alkyl derivative of arginine is $N^\alpha$-decylarginine.

16. A method for inhibiting acid production by microorganisms in the oral cavity which comprises introducing into the oral cavity in a pharmaceutically acceptable carrier, an effective amount of an $N^\alpha$-alkyl derivative of arginine having the formula:

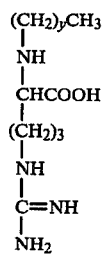

wherein y is an integer of from 6 to 29, or a pharmaceutically acceptable salt thereof.

17. A method for inhibiting acid production by microorganisms in the oral cavity which comprises introducing into the oral cavity a composition comprising, in a pharmaceutically acceptable carrier, from about 0.0001% to about 10% of a fluoride salt and an effective amount of an $N^\alpha$-alkyl derivative of arginine having the formula:

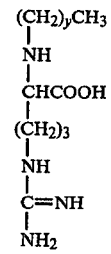

wherein y is an integer of from 6 to 29, or a pharmaceutically acceptable salt thereof.

18. A method for inhibiting acid production by microorganisms in the oral cavity which comprises introducing into the oral cavity a composition comprising from about 0.05 to about 10% of $N^\alpha$-alkyl derivative of arginine having the formula:

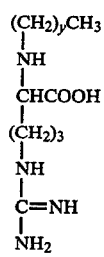

wherein y is an integer of from 6 to 19, or a pharmaceutically acceptable salt thereof, in combination with from about 0.001 to about 1.0% of a fluoride salt in a pharmaceutically acceptable polyol-containing vehicle.

* * * * *